US009161683B2

(12) United States Patent
Sato et al.

(10) Patent No.: US 9,161,683 B2
(45) Date of Patent: Oct. 20, 2015

(54) ELECTRONIC ENDOSCOPIC APPARATUS

(75) Inventors: Takayuki Sato, Tokyo (JP); Kaoru Kotoda, Tokyo (JP); Hisashi Nishimura, Tokyo (JP); Kazuhiro Takizawa, Tokyo (JP); Motoo Azuma, Tokorozawa (JP); Satoshi Tanaka, Tokyo (JP); Naruyasu Kobayashi, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 374 days.

(21) Appl. No.: 13/527,098

(22) Filed: Jun. 19, 2012

(65) Prior Publication Data
US 2012/0320174 A1 Dec. 20, 2012

(30) Foreign Application Priority Data

Jun. 20, 2011 (JP) ................................ 2011-136410

(51) Int. Cl.
*H04N 7/18* (2006.01)
*A61B 1/04* (2006.01)
*A61B 1/00* (2006.01)

(52) U.S. Cl.
CPC ............... *A61B 1/04* (2013.01); *A61B 1/00006* (2013.01)

(58) Field of Classification Search
CPC ........................................................ A61B 1/04
USPC .......................................................... 348/65
See application file for complete search history.

(56) References Cited

U.S. PATENT DOCUMENTS

| 4,831,444 | A | 5/1989 | Kato |
| 5,255,092 | A | 10/1993 | Loonen |
| 5,585,840 | A | 12/1996 | Watanabe et al. |
| 6,765,706 | B2 | 7/2004 | Tokuda et al. |
| 7,248,281 | B2 * | 7/2007 | Abe ................................. 348/65 |
| 7,420,586 | B2 * | 9/2008 | Higuchi .......................... 348/65 |

(Continued)

FOREIGN PATENT DOCUMENTS

| JP | 2001-070241 A | 3/2001 |
| JP | 2001-275956 A | 10/2001 |

(Continued)

OTHER PUBLICATIONS

Japanese Office Action dated Feb. 3, 2015, issued in corresponding JP Patent Application No. 2011-136410 with English translation (4 pages).

(Continued)

*Primary Examiner* — William C Vaughn, Jr.
*Assistant Examiner* — Luis Perez Fuentes
(74) *Attorney, Agent, or Firm* — Westerman, Hattori, Daniels & Adrian, LLP

(57) ABSTRACT

A CMOS sensor converts optical information into an electric signal, and outputs the converted electric signal as an image signal. An imaging clock generating unit generates an imaging clock acting as a source of a drive signal that drives the CMOS sensor. A drive signal generating unit generates an imaging synchronization signal and a drive signal based on the imaging clock. A display clock generating unit generates a display clock. A display synchronization signal generating unit generates a display synchronization signal based on the display clock. A phase comparing unit compares a phase of the imaging synchronization signal with a phase of the display clock, and controls oscillation of the display clock generating unit based on a result of the comparison.

8 Claims, 12 Drawing Sheets

(56) References Cited

U.S. PATENT DOCUMENTS

| | | | |
|---|---|---|---|
| 7,485,091 B2 * | 2/2009 | Abe | 600/109 |
| 7,801,586 B2 * | 9/2010 | Muratayev et al. | 600/407 |
| 7,855,727 B2 | 12/2010 | Adler et al. | |
| 8,248,464 B2 | 8/2012 | Takahashi | |
| 8,380,289 B2 * | 2/2013 | Zellers et al. | 600/426 |
| 8,558,880 B2 * | 10/2013 | Nambakam et al. | 348/74 |
| 8,970,686 B2 * | 3/2015 | Kobayashi et al. | 348/65 |
| 2005/0093972 A1 | 5/2005 | Higuchi | |
| 2006/0055793 A1 * | 3/2006 | Adler et al. | 348/211.99 |
| 2011/0048764 A1 | 3/2011 | Hira et al. | |
| 2012/0320175 A1 * | 12/2012 | Takizawa et al. | 348/65 |
| 2012/0320176 A1 * | 12/2012 | Tanaka et al. | 348/65 |
| 2012/0320177 A1 | 12/2012 | Nishimura et al. | |
| 2013/0016199 A1 * | 1/2013 | Kobayashi et al. | 348/65 |

FOREIGN PATENT DOCUMENTS

| | | |
|---|---|---|
| JP | 2004-049770 A | 2/2004 |
| JP | 2005-305124 A | 11/2005 |
| JP | 2006-288753 A | 10/2006 |
| JP | 2007-295096 A | 11/2007 |
| JP | 2009-061032 A | 3/2009 |
| JP | 2009-201540 A | 9/2009 |

OTHER PUBLICATIONS

Non Final Office Action dated Oct. 23, 2014, issued in U.S. Appl. No. 13/527,113 (18 pages).
Non Final Office Action dated Nov. 7, 2014 issued in U.S. Appl. No. 13/528,226 (16 pages).
Notice of Allowance dated Apr. 24, 2015, issued in U.S. Appl. No. 13/527,113 (11 pages).
Final Office Action dated Jun. 5, 2015 issued in U.S. Appl. No. 13/528,226 (17 pages).
Notice of Reasons for Rejection dated Feb. 3, 2015, issued in Japanese Patent Application No. 2011-136407 with English translation (4 pages).
Notice of Reasons for Rejection dated Feb. 3, 2015, issued in Japanese Patent Application No. 2011-136408 with English translation (4 pages).

* cited by examiner

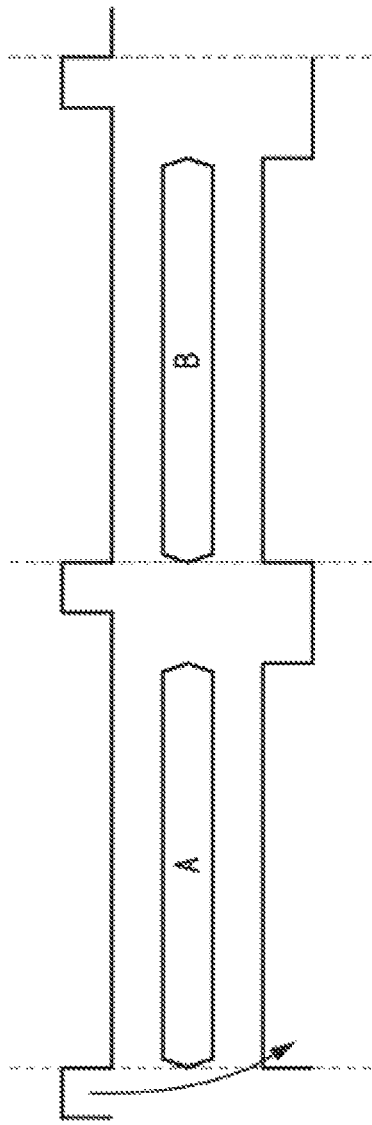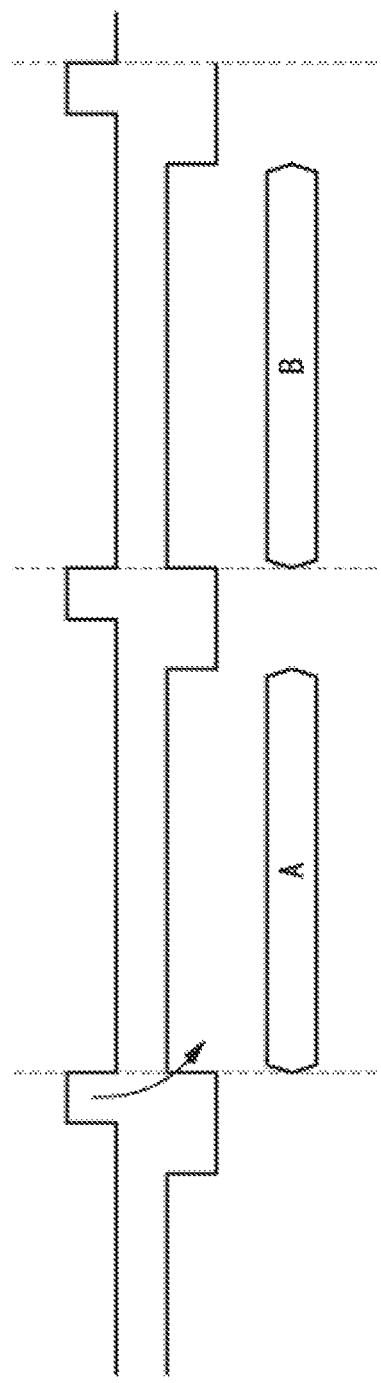

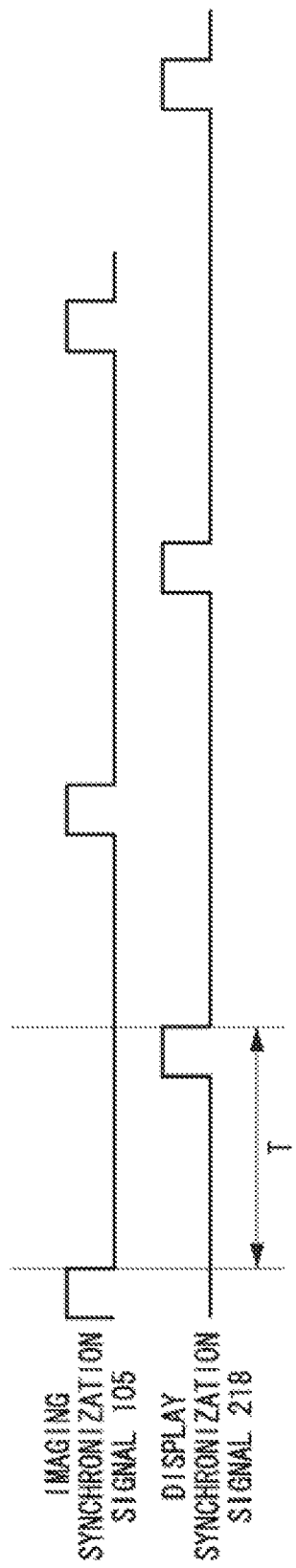

ELECTRONIC ENDOSCOPIC APPARATUS

BACKGROUND OF THE INVENTION

1. Field of the Invention

The present invention relates to an electronic endoscopic apparatus that includes an endoscopic scope on which a solid-state imaging device is mounted and an image processing processor performing predetermined image processing on an image signal from the endoscopic scope.

Priority is claimed on Japanese Patent Application No. 2011-136410 filed on Jun. 20, 2011, the content of which is incorporated herein by reference.

2. Description of Related Art

With the recent advancement of semiconductor technology, solid-state imaging devices such as Charge-Coupled Devices (CCD) or Complementary Metal Oxide Semiconductor (CMOS) sensors are moving toward higher pixels.

Electronic endoscopes on which solid-state imaging devices are mounted are no exception to this trend, and the electronic endoscopes are moving toward higher definition.

With the trend toward higher pixels in the solid-state imaging devices, a frequency of a clock signal required for image processing increases as well, and various phenomena take place. For example, in the electronic endoscopes, a distal end of an endoscopic scope on which the solid-state imaging device is mounted is separated from an image processing processor performing image processing. For this reason, a transmission line between the endoscopic scope and the image processing processor may be subjected to signal degradation. When a signal transmitted between the endoscopic scope and the image processing processor increases in frequency, the signal degradation becomes greater. Because of the high-frequency signal traveling through the transmission line, leakage of electromagnetic waves also becomes more prominent.

An electronic endoscopic apparatus is proposed in Japanese Unexamined Patent. Application, First Publication No. 2001-275956. In this electronic endoscopic apparatus, a waveform smoothing circuit is inserted into an output portion of an electronic scope. Due to this waveform smoothing circuit, high-frequency noise released between the electronic scope and a processor device is inhibited.

Japanese Unexamined Patent Application, First Publication No. 2001-275956 contains no teaching in terms of synchronization between an endoscopic scope and a monitor instrument. Since a solid-state imaging device having various angles of view depending on a target to be observed and use is mounted on the endoscopic scope, an operating frequency and an angle of view are different according to the endoscopic scope. Accordingly, to display an image captured by the endoscopic scope on the monitor, frequency conversion adapted to a synchronization signal of the monitor is required.

Depending on a relationship between a display clock and an imaging clock, there is a subtle difference between a cycle in which the endoscopic scope captures an image of one frame and a cycle in which the monitor instrument displays an image of one frame. As such, both cycles are gradually shifted in phase. Further, when the phase shift between the cycles exceeds a time of one frame, a phenomenon called "passing" or "frame dropping" takes place.

FIG. 13 schematically shows a relation between a one-frame cycle based on an imaging clock and a one-frame cycle based on a display clock. As shown in FIG. 13, the one-frame cycle based on the imaging clock and the one-frame cycle based on the display clock are subtly different from each other. Accordingly, a shift D0, D1, D2 of the one-frame cycle increases with the passage of time.

SUMMARY OF THE INVENTION

According to a first aspect of the present invention, an electronic endoscopic apparatus includes an image processing processor and an endoscopic scope. The endoscopic scope includes a solid-state imaging device configured to convert optical information into an electric signal and output the converted electric signal as an image signal, an imaging clock generating unit configured to generate an imaging clock acting as a source of a drive signal that drives the solid-state imaging device, and a drive signal generating unit configured to generate an imaging synchronization signal and the drive signal based on the imaging clock. The image processing processor includes a display clock generating unit configured to generate a display clock, a display synchronization signal generating unit configured to generate a display synchronization signal based on the display clock, and a control unit configured to compare a phase of the imaging synchronization signal with a phase of the display clock and control oscillation of the display clock generating unit based on a result of the comparison.

According to a second aspect of the present invention, in the electronic endoscopic apparatus, the imaging clock may have a cycle that is M/N of a cycle of the display synchronization signal (where M and N are natural numbers).

According to a third aspect of the present invention, in the electronic endoscopic apparatus, the endoscopic scope includes a superimposing unit configured to output a superimposition signal by superimposing the image signal and the imaging synchronization signal. The image processing processor includes a synchronization signal restoring unit configured to restore the imaging synchronization signal from the superimposition signal.

According to a forth aspect of the present invention, in the electronic endoscopic apparatus, the endoscopic scope includes a converting unit configured to convert the image signal into a differential signal. The image processing processor includes a demodulating unit configured to demodulate the differential signal into the image signal.

According to a fifth aspect of the present invention, in the electronic endoscopic apparatus, the image processing processor includes a synchronization memory configured to temporarily record the image signal. Writing of the image signal into the synchronization memory is controlled based on the imaging synchronization signal. Readout of the image signal from the synchronization memory is controlled based on the display synchronization signal.

According to a sixth aspect of the present invention, in the electronic endoscopic apparatus, the endoscopic scope includes an electro-optic converting unit configured to convert the image signal into an optical signal. The image processing processor includes a photoelectric converting unit configured to convert the optical signal into the image signal.

According to a seventh aspect of the present invention, in the electronic endoscopic apparatus, the endoscopic scope includes a wireless transmitting unit configured to wirelessly transmit the image signal. The image processing processor includes a wireless receiving unit configured to receive the image signal that is wirelessly transmitted by the wireless transmitting unit.

According to an eighth aspect of the present invention, in the electronic endoscopic apparatus, the endoscopic scope includes a compressing unit configured to compress the image signal. The image processing processor includes a decompressing unit configured to expand the image signal compressed by the compressing unit.

According to a ninth aspect of the present invention, in the electronic endoscopic apparatus, the endoscopic scope outputs scope type information indicating a type thereof. The image processing processor includes an identifying unit configured to identify the type of the endoscopic scope with reference to the scope type information, a second imaging clock generating unit configured to generate a second imaging clock acting as a source of a second drive signal that drives the solid-state imaging device, a second drive signal generating unit configured to generate a second imaging synchronization signal and the second drive signal based on the imaging clock, and an output control unit configured to control whether or not to output the second imaging clock, the second imaging synchronization signal, and the second drive signal to the endoscopic scope based on the type of the endoscopic scope which is identified by the identifying unit.

BRIEF DESCRIPTION OF THE DRAWINGS

FIG. 6A is a timing chart that explains control of writing and readout of an image signal with respect to a synchronization memory included in the electronic endoscopic apparatus according to the second embodiment of the present invention.

FIG. 6B is a timing chart that explains control of writing and readout of an image signal with respect to a synchronization memory included in the electronic endoscopic apparatus according to the second embodiment of the present invention.

FIG. 7 is a timing chart showing an imaging synchronization signal and a display synchronization signal in the second embodiment of the present invention.

DETAILED DESCRIPTION OF THE PREFERRED EMBODIMENTS

Hereinafter, embodiments of the present invention will be described with reference to the drawings.

First Embodiment

Figure 1:
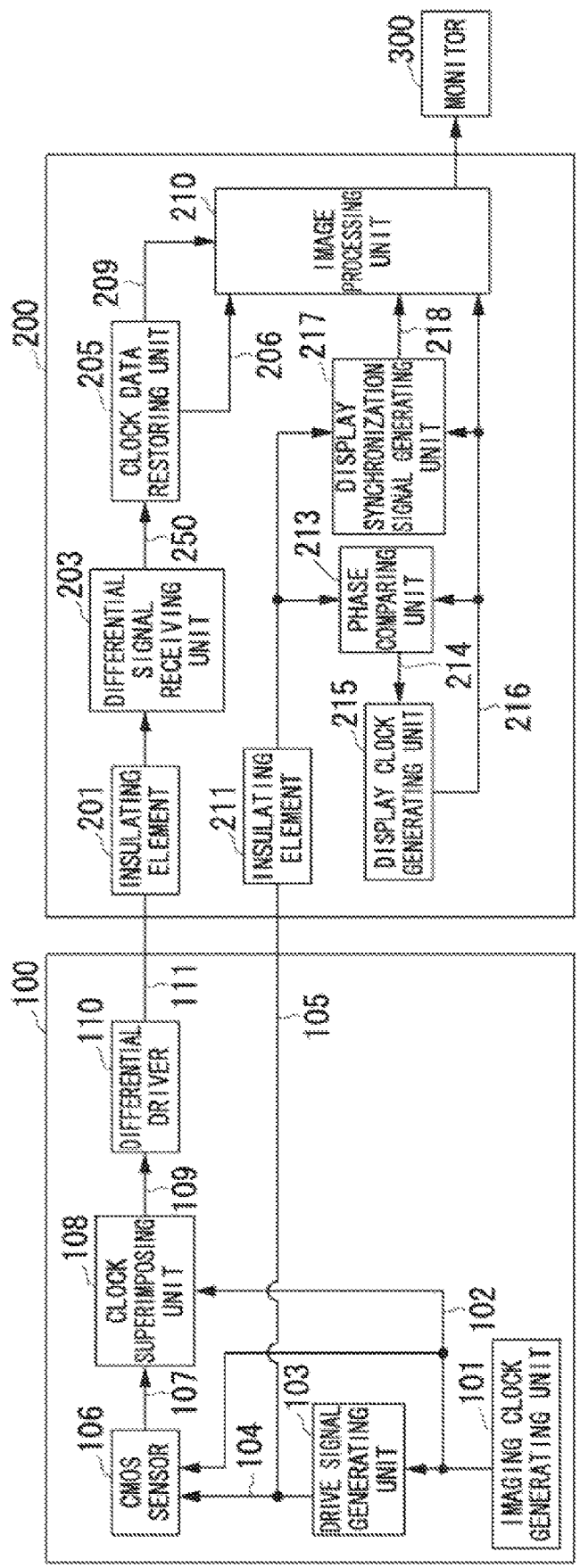
FIG. 1 is a block diagram showing a configuration of an electronic endoscopic apparatus according to a first embodiment of the present invention.

First, a first embodiment of the present invention will be described. FIG. 1 shows a configuration of an electronic endoscopic apparatus according to the present embodiment. As shown in FIG. 1, the electronic endoscopic apparatus includes an endoscopic scope 100 and an image processing processor 200. The image processing processor 200 is connected to a monitor 300.

The endoscopic scope 100 includes an imaging clock generating unit 101, a drive signal generating unit 103, a complementary metal oxide semiconductor (CMOS) sensor 106, a clock superimposing unit 108, and a differential driver 110. The image processing processor 200 includes insulating elements 201 and 211, a differential signal receiving unit 203, a clock data restoring unit 205, an image processing unit 210, a phase comparing unit 213, a display clock generating unit 215, and a display synchronization signal generating unit 217.

In the endoscopic scope 100, the imaging clock generating unit 101 generates an imaging clock 102 acting as a source of a drive signal 104 that drives the CMOS sensor 106. The imaging clock 102 has the same frequency as a display clock 216 to be described later. The drive signal generating unit 103 generates the drive signal 104 using the imaging clock 102 as an operation clock. Here, the drive signal 104 includes synchronization signals, and an imaging synchronization signal 105 which indicates start of one frame among the synchronization signals, is output to the image processing processor 200 as well. The CMOS sensor 106 converts optical information into an electric signal according to the imaging clock 102 and the drive signal 104, thereby generating an image signal 107. The clock superimposing unit 108 generates a superimposition signal 109 by superimposing the imaging clock 102 on the image signal 107.

Figure 2:
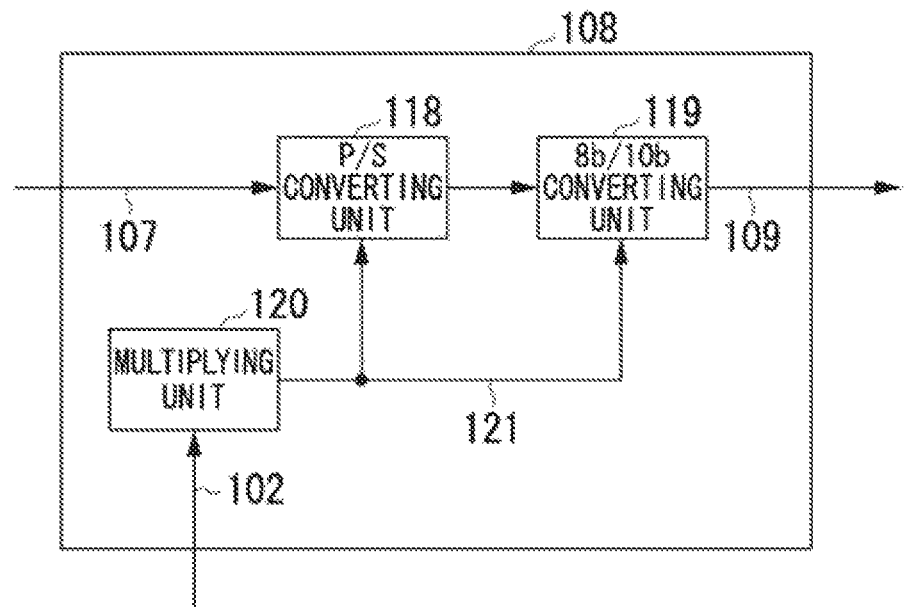
FIG. 2 is a block diagram showing a configuration of a clock superimposing unit included in the electronic endoscopic apparatus according to the first embodiment of the present invention.

FIG. 2 shows a configuration of the clock superimposing unit 108. As shown in FIG. 2, the clock superimposing unit 108 includes a multiplying unit 120, a parallel-to-serial (P/S) converting unit 118, and an 8b/10b converting unit 119. The multiplying unit 120 multiplies the imaging clock 102, and outputs the multiplied imaging clock 102 as a multiplication clock 121 to the P/S converting unit 118 and the 8b/10b converting unit 119. The P/S converting unit 118 converts the image signal 107 from a parallel system into a serial system according to the multiplication clock 121, and outputs the converted serial signal to the 8b/10b converting unit 119. The 8b/10b converting unit 119 allocates redundant data such that the same signal level does not continue over a predetermined time within the input serial signal, encodes a signal including data for clock reproduction, and outputs the superimposition signal 109 on which the multiplication clock 121 is superimposed.

The differential driver 110 converts the superimposition signal 109 output from the clock superimposing unit 108 into a differential signal 111. The differential signal 111 output from the differential driver 110 is input to the image processing processor 200 through a transmission cable of the endoscopic scope 100.

In the image processing processor 200, the input differential signal 111 travels through the insulating element 201, and is received by the differential signal receiving unit 203. The differential signal receiving unit 203 demodulates the received differential signal 111 into a superimposition signal 250. The clock data restoring unit 205 separates the superimposition signal 250 into an imaging clock 206 and an image signal 209.

Figure 3:
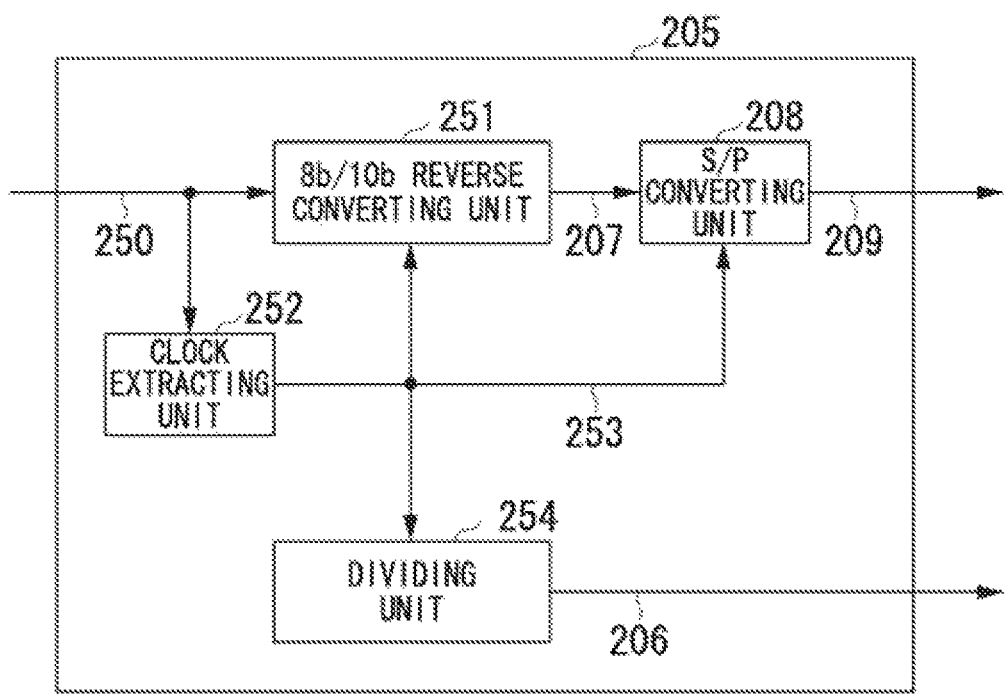
FIG. 3 is a block diagram showing a configuration of a clock data restoring unit included in the electronic endoscopic apparatus according to the first embodiment of the present invention.

FIG. 3 shows a configuration of the clock data restoring unit 205. As shown in FIG. 3, the clock data restoring unit 205 includes a clock extracting unit 252, a dividing unit 254, an 8b/10b reverse converting unit 251, and a serial-to-parallel (S/P) converting unit 208. The clock extracting unit 252 extracts a clock superimposed on the superimposition signal 250, and outputs the extracted clock as an extraction clock 253 to the 8b/10b reverse converting unit 251, the dividing unit 254, and the S/P converting unit 208. The 8b/10b reverse converting unit 251 conducts reverse conversion of the conversion which the aforementioned 8b/10b converting unit 119 has conducted to the superimposition signal 250, and outputs an image signal 207. The dividing unit 254 divides the extraction clock 253, and outputs the divided clock as an imaging clock 206. The S/P converting unit 208 converts the image signal 207 in a serial system into an image signal 209 in a parallel system, and outputs the converted image signal to the image processing unit 210.

The imaging synchronization signal 105 output from the endoscopic scope 100 travels through the insulating element 211, and is input to the phase comparing unit 213 and the display synchronization signal generating unit 217. The display clock generating unit 215 generates a display clock 216 that drives each component pertaining to displaying. The phase comparing unit 213 compares a phase of the imaging synchronization signal 105 with a phase of the display clock 216, and outputs an adjustment signal 214 for controlling an oscillation state of the display clock 216 in the display clock generating unit 215 based on a result of the comparison. The display clock generating unit 215 controls a frequency of the display clock 216 based on the adjustment signal 214 so as to match the phase of the display clock 216 and the phase of the imaging synchronization signal 105. Since there is an oscillator that can arbitrarily change a frequency using an external control signal, such an oscillator may be used to mount the display clock generating unit 215.

Figure 4:
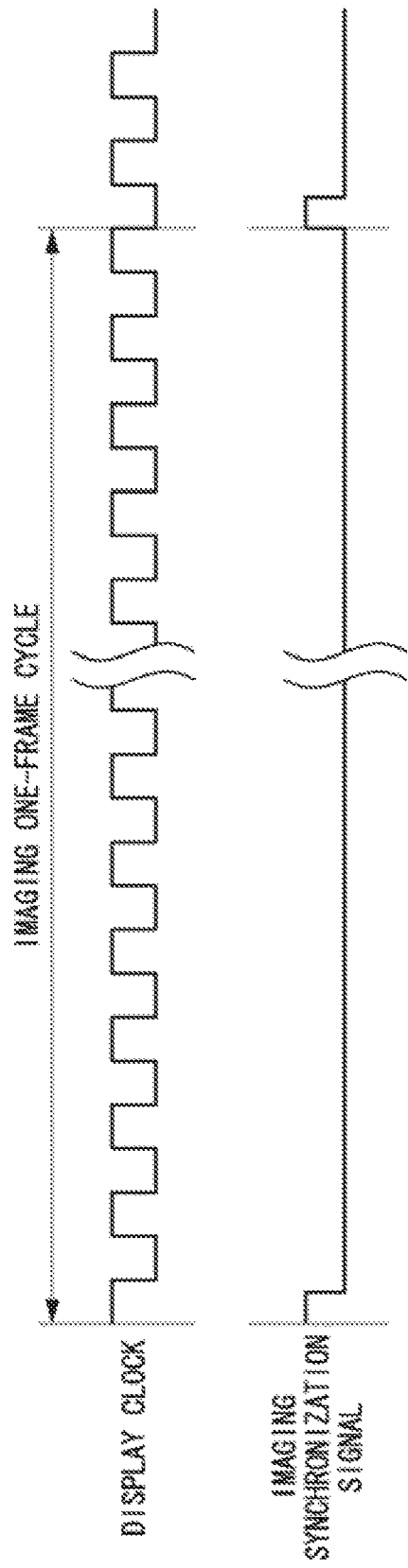
FIG. 4 is a timing chart that explains an operation of a phase comparing unit mounted in the electronic endoscopic apparatus according to the first embodiment of the present invention.

FIG. 4 shows operations of the phase comparing unit 213. The phase comparing unit 213 compares, for instance, a position of a rising edge of the display clock 216 with a position of a rising edge of the imaging synchronization signal 105 (vertical synchronization signal in an example of FIG. 2). Based on a difference between the edge positions, the phase comparing unit 213 outputs the adjustment signal 214 to the display clock generating unit 215. Based on the adjustment signal 214, the display clock generating unit 215 controls the oscillation state of the display clock 216, i.e. the frequency of the display clock 216. Thereby, the position of the rising edge of the display clock 216 is identical to the position of the rising edge of the imaging synchronization signal 105, and the synchronization between the display clock 216 and the imaging synchronization signal 105 can be secured. In FIG. 4, the example in which the vertical synchronization signal is used when the phase thereof is compared with the phase of the display clock 216 is shown. However, a horizontal synchronization signal may be used.

The display synchronization signal generating unit 217 generates a display synchronization signal 218 that complies with television standards to display an image on the monitor 300 for displaying. In this case, the imaging synchronization signal 105 is referred to for matching up one-frame start timings at the imaging side and the displaying side.

The image processing unit 210 switches a clock for processing the image signal 209 from the imaging clock 206 to the display clock 216 using a buffer memory (so-called clock transfer), and performs a variety of image processing for displaying an image on the image signal 209. In this case, the display synchronization signal 218 is referred to as a signal that defines a start position of a frame. In the present embodiment, since the one-frame start timings at the imaging side and the displaying side are matched by the imaging synchronization signal 105, a capacity of the buffer memory required for the clock transfer may be small. The image signal processed by the image processing unit 210 is output to the monitor 300, and is used to display an image on the monitor 300.

In the present embodiment, since the display clock 216 is generated so as to be synchronized with the imaging synchronization signal 105 generated from the imaging clock 102, a phenomenon in which the imaging side and the displaying side have a difference in one-frame time does not occur.

In the present embodiment, various modifications are possible. For example, in the present embodiment, the frequency of the imaging clock is equal to that of the display clock, but the frequency of the imaging clock may be a frequency that meets conditions that a signal having the same cycle as the display synchronization signal can be generated. For example, when a display size is 100×100 and a size of the imaging device is 50×50, the frequency of the imaging clock may be ¼ of the frequency of the display clock. The present embodiment is not limited to this. The frequency (or cycle) of the imaging clock may be M/N of the frequency (or cycle) of the display clock or the frequency (or cycle) of the display synchronization signal according to the display size and the imaging device size (where M and N are natural numbers).

Further, in the present embodiment, the CMOS sensor is used as a solid-state imaging device, but a charge-coupled device (CCD) may be used. Further, a variety of processing circuits may be mounted on the same chip that the CMOS sensor is mounted. Accordingly, the drive signal generating unit 103 and the clock superimposing unit 108 of the present embodiment may be mounted on the same chip that the CMOS sensor is mounted.

As described above, according to the present embodiment, the phase comparing unit 213 compares the phase of the imaging synchronization signal 105 with the phase of the display clock 216, and controls the oscillation state of the display clock 216 based on a result of the comparison. Thereby, the imaging synchronization signal 105 and the display clock 216 can be synchronized with each other. The display synchronization signal generating unit 217 generates the display synchronization signal 218 from the display clock 216 synchronized with the imaging synchronization signal 105. Therefore, the one-frame cycle for imaging is identical to the one-frame cycle for displaying, and thus it is possible to secure synchronization between the imaging and the displaying.

Further, in the present embodiment, the frequency of the imaging clock 102 generated by the imaging clock generating unit 101 and the frequency of the display clock generated by the display clock generating unit 215 need not be the same.

When a ratio between the frequency (or cycle) of the imaging clock and the frequency (or cycle) of the display clock or the frequency (or cycle) of the display synchronization signal is a simple integer ratio, a multiplying circuit and a dividing circuit are added, and thereby the frequencies of the imaging clock and the frequencies of the display clock after being multiplied or divided can be identical to each other.

Further, it is possible to enhance resistance to disturbance noise by using the differential signal to transmit the image signal. Furthermore, since a signal can be transmitted between the endoscopic scope 100 and the image processing processor 200 with small amplitude, high-speed transmission is possible.

Second Embodiment

Figure 5:
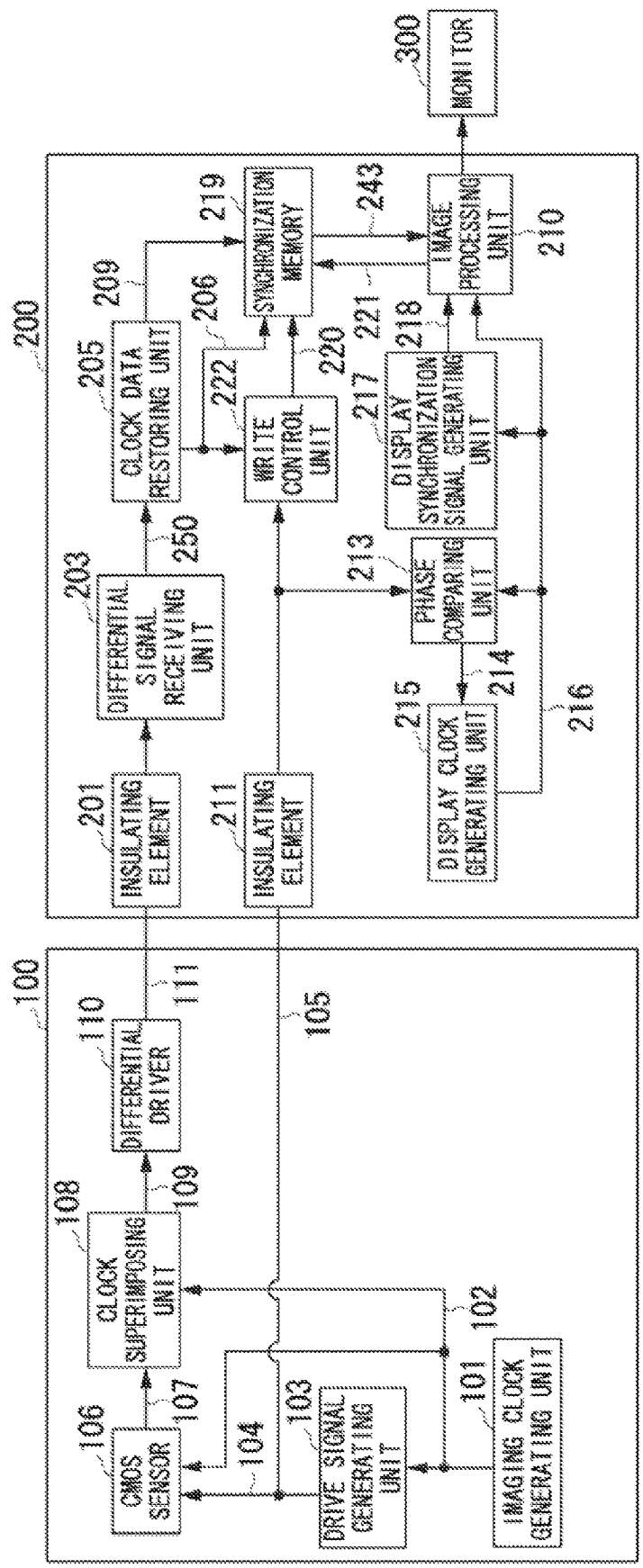
FIG. 5 is a block diagram showing a configuration of an electronic endoscopic apparatus according to a second embodiment of the present invention.

Next, a second embodiment of the present invention will be described. FIG. 5 shows a configuration of an electronic endoscopic apparatus according to the present embodiment. In FIG. 5, components having the same functions as those in the first embodiment are assigned the same symbols, and so description thereof will be omitted.

The present embodiment is different from the first embodiment in that an imaging synchronization signal 105 is not input to a display synchronization signal generating unit 217 and in that the display synchronization signal generating unit 217 independently generates a display synchronization signal 218 without reference to the imaging synchronization signal 105. Further, since the synchronization signal is uniquely generated at an imaging side and a displaying side, a synchronization memory 219 and a write control unit 222 are provided to match up frame start timings of the imaging side and the displaying side. The synchronization memory 219 is configured, for instance, as a frame memory, and temporarily stores an image signal 209. The write control unit 222 controls writing of the image signal 209 to the synchronization memory 219.

As shown in FIG. 6A, in the present embodiment, according to a write control signal 220 which the write control unit 222 generates based on the imaging synchronization signal 105, the image signal 209 is written to the synchronization memory 219. On the other hand, as shown in FIG. 6B, an image processing unit 210 reads out an image signal 243 from the synchronization memory 219 according to a readout control signal 221 generated based on the display synchronization signal 218, and performs predetermined image processing on the read image signal 243.

When the electronic endoscopic apparatus is configured to uniquely generate the synchronization signal at the imaging side and the displaying side, a mechanism of generating the synchronization signal can be simplified. However, as shown in FIG. 7, since a start timing of an imaging-side frame indicated by the imaging synchronization signal 105 is different from a start timing of a displaying-side frame indicated by the display synchronization signal 218, a time T that is a time difference between the each start timing becomes different whenever the electronic endoscopic apparatus is started. In the present embodiment, the image signal 209 is first stored in the synchronization memory 219, and the image signal 243 is read out from the synchronization memory 219 on the basis of the display synchronization signal 218. Thereby, it is possible to display an image synchronized to the displaying side regardless of the synchronization signal of the imaging side. Further, since the display synchronization signal 218 is generated regardless of the imaging synchronization signal 105, the synchronization of the displaying side is not disturbed even when the endoscopic scope is extracted and replaced.

As described above, according to the present embodiment, since the display synchronization signal 218 can be generated without reference to the imaging synchronization signal 105, the display synchronization signal generating unit 217 is allowed to have a simple configuration. Further, the displayed image is not disturbed when the endoscopic scope 100 is inserted and extracted.

Third Embodiment

Figure 8:
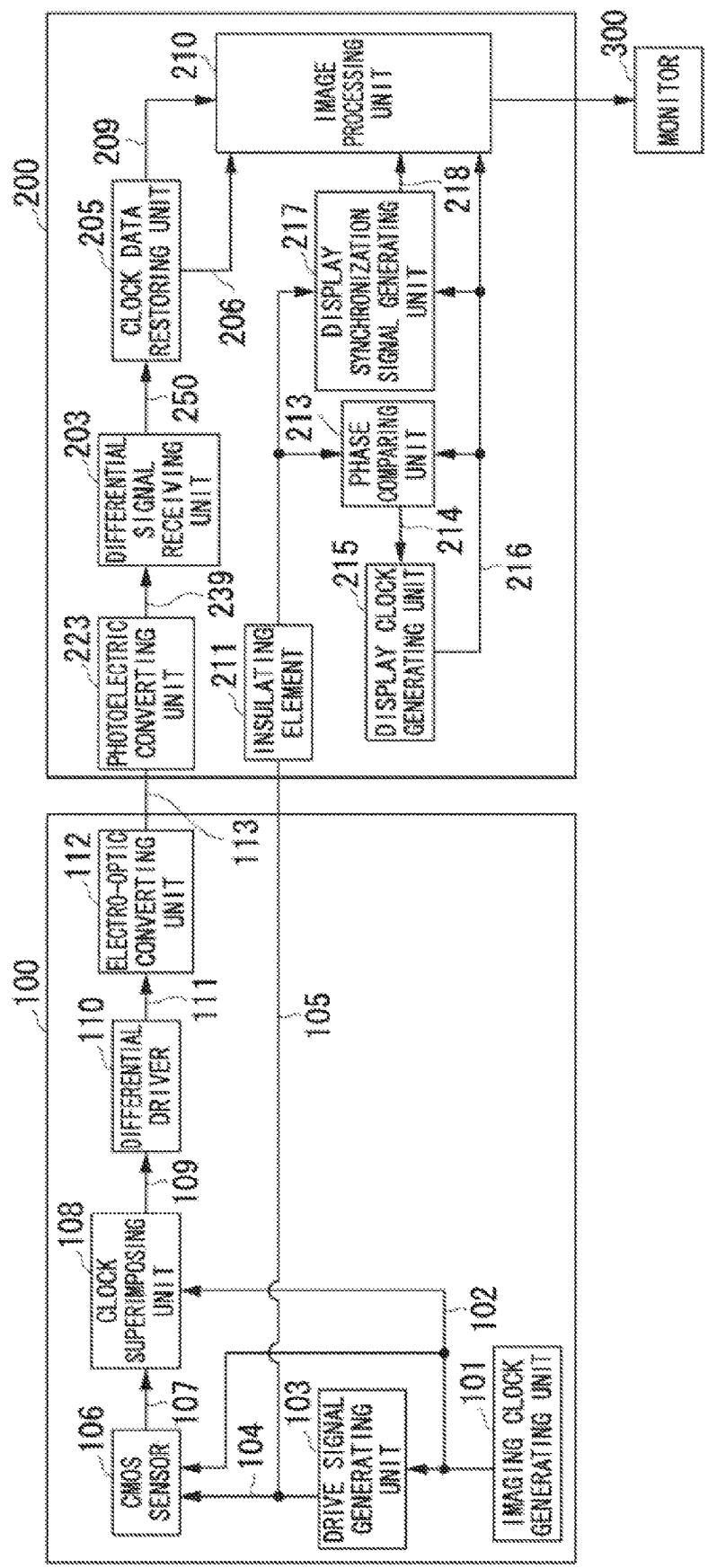
FIG. 8 is a block diagram showing a configuration of an electronic endoscopic apparatus according to a third embodiment of the present invention.

Next, a third embodiment of the present invention will be described. FIG. 8 shows a configuration of an electronic endoscopic apparatus according to the present embodiment. In FIG. 8, components having the same functions as those in the first and second embodiments are assigned the same symbols, and so description thereof will be omitted.

The present embodiment is different from the first embodiment in that an electro-optic converting unit 112 is added to an endoscopic scope 100, in that a photoelectric converting unit 223 is added to an image processing processor 200, and in that an image signal is transmitted as an optical signal between the endoscopic scope 100 and the image processing processor 200.

In the endoscopic scope 100, the electro-optic converting unit 112 converts a differential signal 111 into an optical signal 113. The optical signal 113 output from the electro-optic converting unit 112 is input to the image processing processor 200. In the image processing processor 200, the photoelectric conversion unit 223 converts the input optical signal 113 into a differential signal 239 again. Afterwards, similar to the first embodiment, image processing is performed by an image processing unit 210, and an image is displayed on a monitor 300.

In the present embodiment, various modifications are possible. For example, a position in which the electro-optic converting unit 112 is mounted may be the inside of the endoscopic scope 100, and may be any one of a distal end of the endoscopic scope 100, a joint between the endoscopic scope 100 and the image processing processor 200, and an operating portion in which a user performs various operations. Further, when the electro-optic converting unit 112 can be arranged around a CMOS sensor 106, a differential driver 110 and a differential signal receiving unit 203 may not be provided.

As described above, according to the present embodiment, the image signal is transmitted as the optical signal between the endoscopic scope 100 and the image processing processor 200. Thereby, it is possible to expect to improve resistance to electrical noise and to reduce electromagnetic noise. Further, an insulating process for securing the safety of a examinee becomes easy.

Fourth Embodiment

Figure 9:
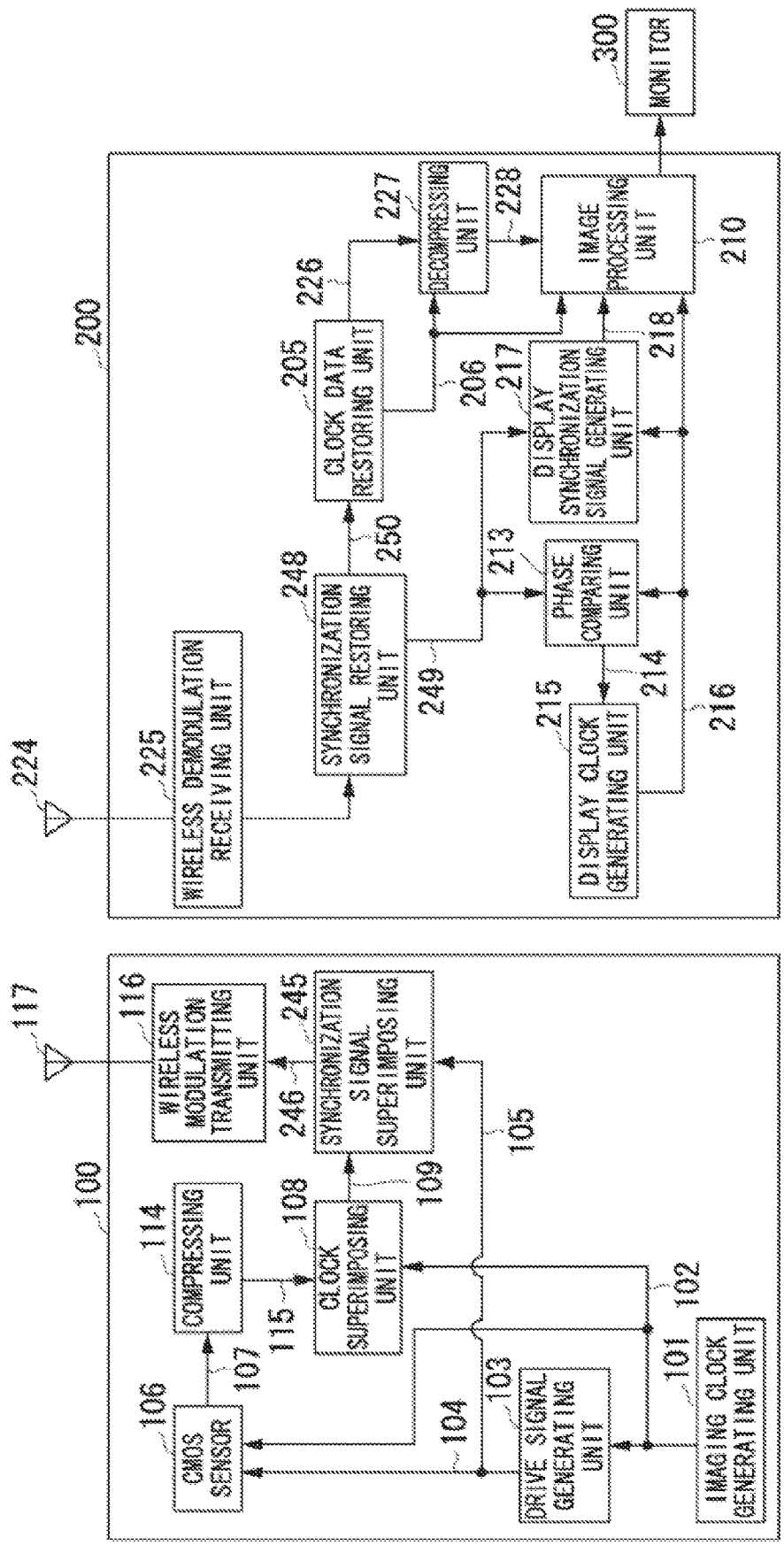
FIG. 9 is a block diagram showing a configuration of an electronic endoscopic apparatus according to a fourth embodiment of the present invention.

Next, a fourth embodiment of the present invention will be described. FIG. 9 shows a configuration of an electronic endoscopic apparatus according to the present embodiment. In FIG. 9, components having the same functions as those in the first, second and third embodiments are assigned the same symbols, and so description thereof will be omitted.

The present embodiment is different from the first embodiment in terms of the following. A compressing unit 114, a synchronization signal superimposing unit 245, a wireless modulation transmitting unit 116, and an antenna 117 are added to an endoscopic scope 100. An antenna 224, a wireless demodulation receiving unit 225, a synchronization signal restoring unit 248, and a decompressing unit 227 are added to an image processing processor 200. An image signal is transmitted as a wireless signal between the endoscopic scope 100 and the image processing processor 200.

In the endoscopic scope 100, the compressing unit 114 compresses an image signal 107 from a CMOS sensor 106, and outputs a compression signal 115. A clock superimposing unit 108 superimposes an imaging clock 102 on the compression signal 115, and outputs a superimposition signal 109. The synchronization signal superimposing unit 245 allocates an imaging synchronization signal 105 to the superimposition signal 109 as a predetermined bit pattern, and outputs a synchronization superimposition signal 246. For example, since a signal undergoing 8$b$/10$b$ conversion is always subjected to a change in the signal level thereof within three clocks, the same signal is allocated for four or more clocks to the signal undergoing 8$b$/10$b$ conversion. Thereby, a portion at which the same signal continues for four or more clocks can be recognized as a synchronization signal. The wireless modulation transmitting unit 116 modulates the synchronization superimposition signal 246, and transmits the modulated signal to the image processing processor 200 via the antenna 117 as wireless data.

In the image processing processor 200, the wireless demodulation receiving unit 225 receives wireless data via the antenna 224, and demodulates the received wireless data. The synchronization signal restoring unit 248 detects a bit pattern of the portion at which the same signal continues for four or more clocks within a received signal, and restores an imaging synchronization signal 249. Further, the synchronization signal restoring unit 248 outputs a superimposition signal 250 in which a signal of a portion corresponding to the imaging synchronization signal 249 is excepted from the received signal.

The clock data restoring unit 205 divides the superimposition signal 250 into a compression signal 226 and an imaging clock 206. The decompressing unit 227 expands the compression signal 226 to restore an image signal 228. Afterwards, similar to the first embodiment, image processing is performed by an image processing unit 210, and an image is displayed on a monitor 300.

As described above, according to the present embodiment, by providing wireless connection between the endoscopic scope 100 and the image processing processor 200, the mutual connection using a cable is not necessary. For this reason, the number of cables required for data transmission can be reduced, and the endoscopic scope can be reduced in diameter. Further, similar to the third embodiment, since the wireless transmission can realize insulation in itself, the number of insulating elements can be reduced.

Further, the imaging synchronization signal 105 and the image signal are superimposed and transmitted on the same transmission line. Thereby, since the transmission line for the imaging synchronization signal can be omitted, the endoscopic scope can be further reduced in diameter. Furthermore, the compressing and expanding processes are applied, so that an amount of data to be transmitted can be reduced, and particularly a stable operation of wireless communication can be realized.

In the first and second embodiments, the imaging synchronization signal 105 and the image signal may be superimposed and transmitted on the same transmission line as in the present embodiment. Further, in the first and second embodiments, the compression and expansion of the image signal may also be performed as in the present embodiment.

Fifth Embodiment

Figure 10:
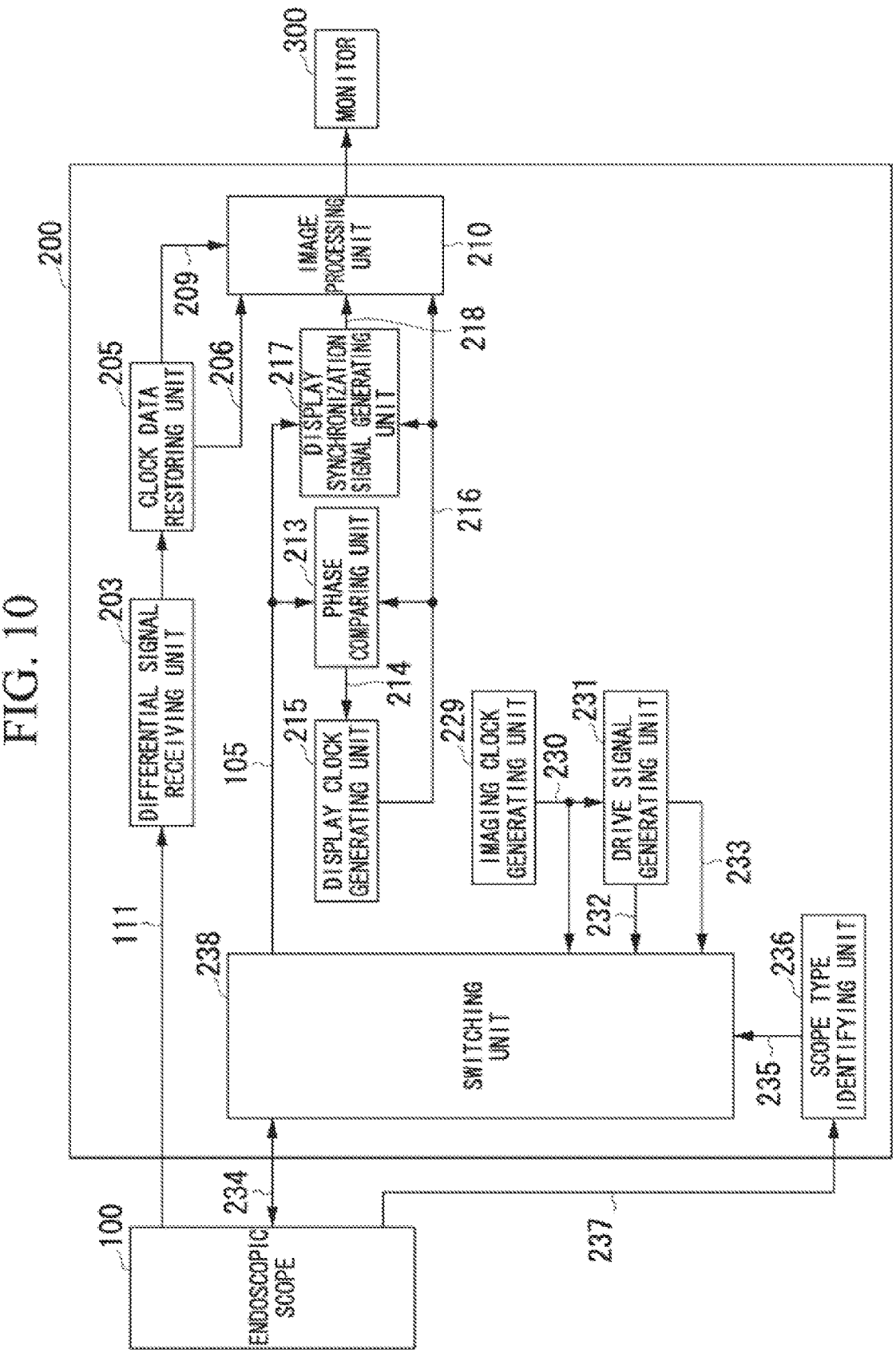
FIG. 10 is a block diagram showing a configuration of an electronic endoscopic apparatus according to a fifth embodiment of the present invention.

Next, a fifth embodiment of the present invention will be described. FIG. 10 shows a configuration of an electronic endoscopic apparatus according to the present embodiment. In FIG. 10, components having the same functions as those in the first, second and third embodiments are assigned the same symbols, and so description thereof will be omitted.

In the present embodiment, an imaging clock generating unit 229, a drive signal generating unit 231, a scope type identifying unit 236, and a switching unit 238 are added to an image processing processor 200. The imaging clock generating unit 229 generates an imaging clock 230. The drive signal generating unit 231 generates an imaging synchronization signal 232 and a drive signal 233 using the imaging clock 230 as an operation clock. The scope type identifying unit 236 identifies a type of the connected endoscopic scope 100 based on scope type information 237 that is output from an endoscopic scope 100 and represents a type of a scope, and outputs a switching control signal 235 according to the identified type. The switching unit 238 controls switching of a control signal 234 transmitted between the endoscopic scope 100 and the image processing processor based on the switching control signal 235.

In connection with a method of identifying the type of the endoscopic scope 100, for example, a method that a resistor element which has a specific resistance value depending on the type of the endoscopic scope 100 is provided in the endoscopic scope 100, and measuring the specific resistance value using the scope type identifying unit 236.

Figure 11:
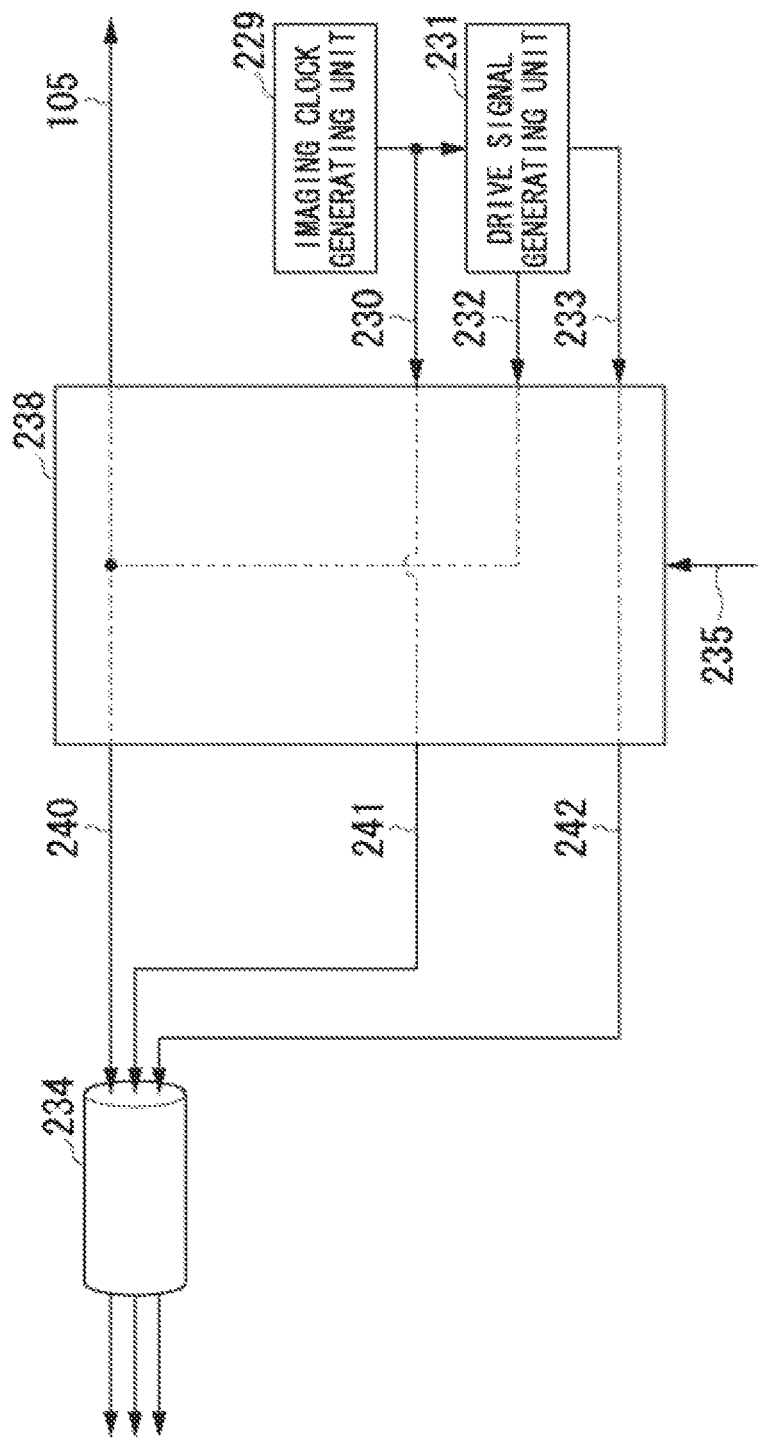
FIG. 11 is a block diagram that explains an operation of a switching unit included in the electronic endoscopic apparatus according to the fifth embodiment of the present invention.

Hereinafter, an operation of the switching unit 238 will be described using FIGS. 11 and 12. The switching signal 234 includes a signal 240, a signal 241, and a signal 242. When the switching control signal 235, which shows that the endoscopic scope 100 without the imaging clock generating unit and the drive signal generating unit is connected, is input to the switching unit 238, as shown in FIG. 11, the switching unit 238 outputs an imaging clock 230, which is generated by the imaging clock generating unit 229 in the image processing processor 200, to the signal 241. Furthermore, the switching unit 238 outputs a drive signal 233 generated by the drive signal generating unit 231 to the signal 242, and outputs an imaging synchronization signal 232 to the signal 240. The endoscopic scope 100 uses the signal 240 as the imaging synchronization signal, the signal 241 as the imaging clock, and the signal 242 as the drive signal.

Further, the switching unit 238 outputs the imaging synchronization signal 232 generated by the drive signal generating unit 231 to the inside of the image processing processor 200 as an imaging synchronization signal 105. As is case with the first embodiment, the imaging synchronization signal 105 is used to make a phase comparison with the display clock in the phase comparing unit 213, and is used to generate the display synchronization signal 218 in the display synchronization signal generating unit 217.

Figure 12:
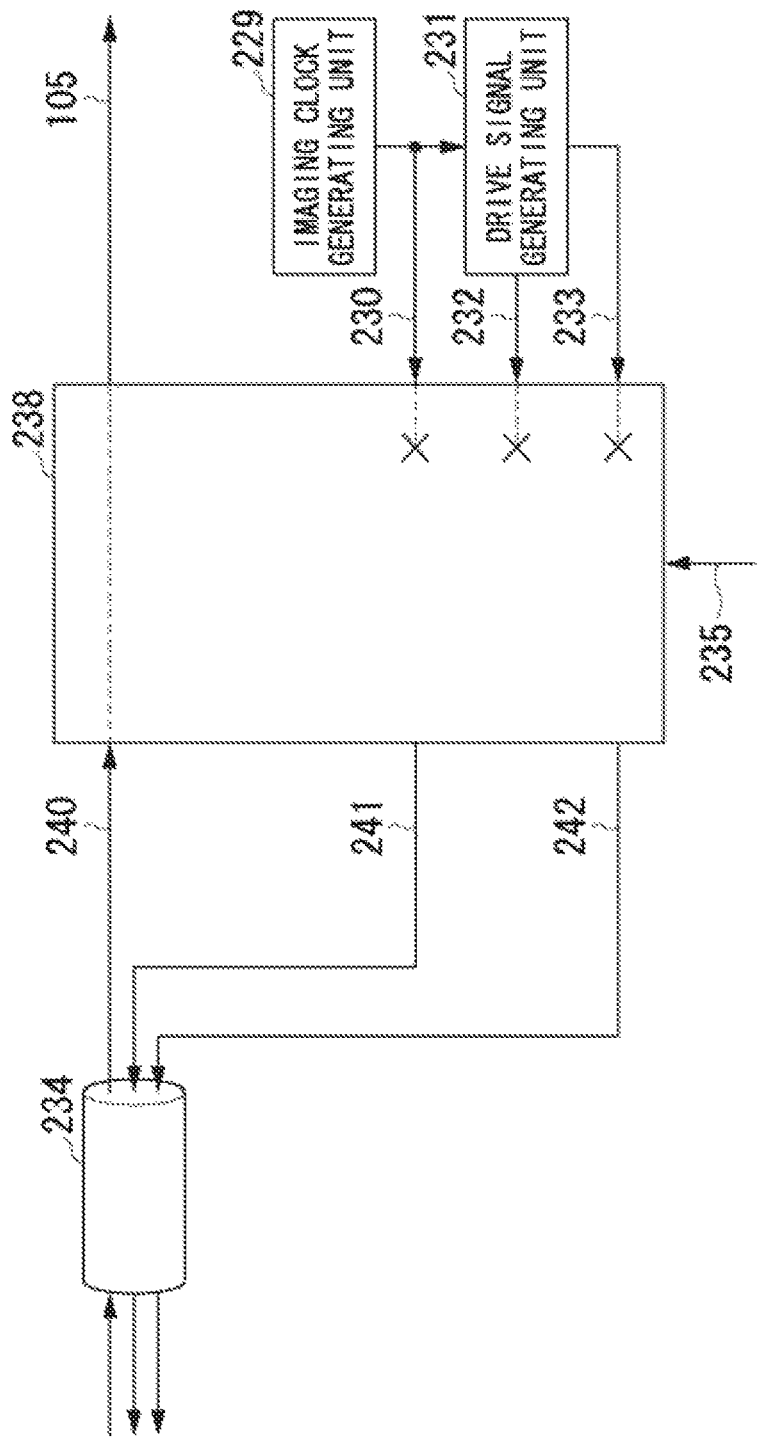
FIG. 12 is a block diagram that explains an operation of the switching unit included in the electronic endoscopic apparatus according to the fifth embodiment of the present invention.
Figure 13:
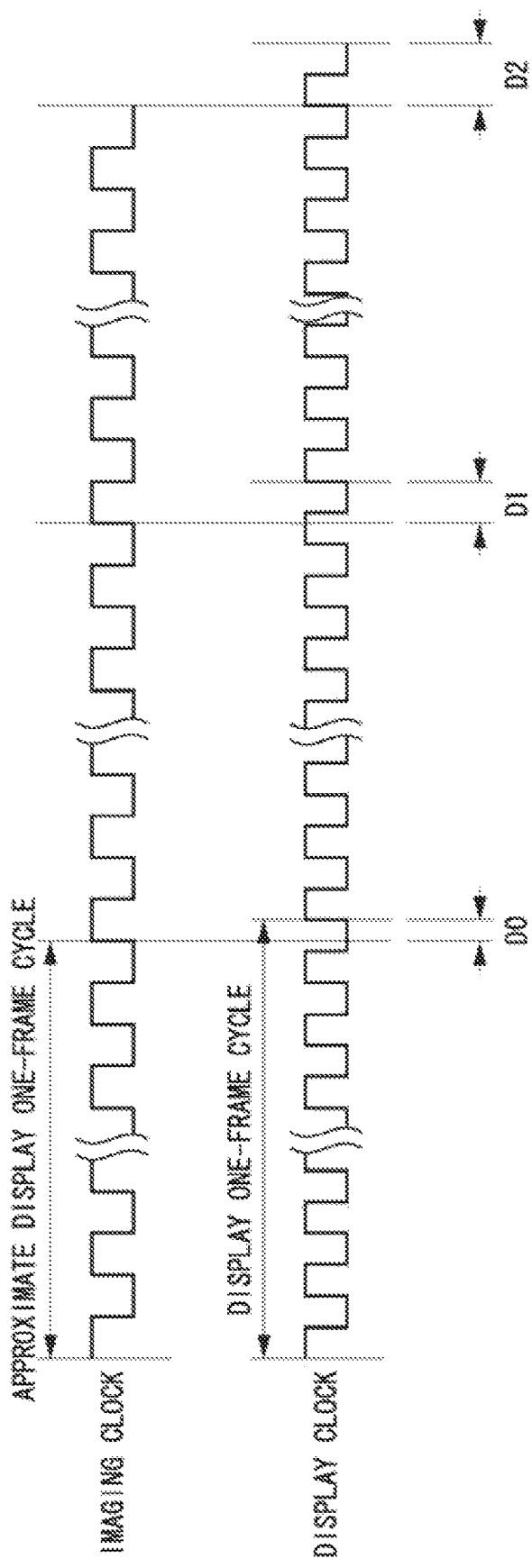
FIG. 13 is a timing chart that explains conventional problems.

On the other hand, when the switching control signal 235, which shows that the endoscopic scope 100 having the imaging clock generating unit and the drive signal generating unit is connected, is input to the switching unit 238, as shown in FIG. 12, the switching unit 238 outputs the signal 240, which is input from the endoscopic scope 100, to the inside of the image processing processor 200 as the imaging synchronization signal 105. In this case, the endoscopic scope 100 shall transmit the imaging synchronization signal as the signal 240. Furthermore, the switching unit 238 cuts off connection between the imaging clock 230 and the signal 241, and connection between the drive signal 233 and the signal 242.

In the present embodiment, various modifications are possible. For example, in the present embodiment, as a means for identifying the type of the endoscopic scope 100, an identifying configuration based on the measurement of the resistance value is used. However, for example, data communication is conducted between the endoscopic scope 100 and the image processing processor 200, and then the type of the endoscopic scope 100 may be determined based on a result of the data communication. Furthermore, in the present embodiment, when the endoscopic scope 100 in which the imaging clock generating unit and the drive signal generating unit are mounted is connected, the outputs of the imaging clock and the drive signal inside the image processing processor 200 are cut off. However, in addition, the oscillation of the imaging clock may be stopped.

As described above, according to the present embodiment, the type of the connected endoscopic scope 100 is identified by the scope type information, and the control signal between the endoscopic scope 100 and the image processing processor 200 is switched. Thereby, both the endoscopic scope of the present invention in which the imaging clock generating unit and the drive signal generating unit are mounted and the endoscopic scope of the related art in which the imaging clock generating unit and the drive signal generating unit are not mounted can be connected to the same image processing processor.

While the embodiments of the present invention have been described in detail with reference to the drawings, specific configurations are not limited to these embodiments, and the present invention includes design modifications within a scope not departing from the scope of the present invention. Accordingly, the invention is not to be considered as being limited by the foregoing description, and is only limited by the scope of the appended claims.

What is claimed is:

1. An electronic endoscopic apparatus comprising:
an image processing processor; and
an endoscopic scope, wherein the endoscopic scope comprises:
a solid-state imaging device configured to convert optical information into an electric signal and output the converted electric signal as an image signal;
an imaging clock generating circuit configured to generate an imaging clock acting as a source of a drive signal that drives the solid-state imaging device;
a drive signal generating circuit configured to generate an imaging synchronization signal and the drive signal based on the imaging clock;
a synchronization signal superimposing circuit configured to output a synchronization superimposition signal by superimposing the image signal and the imaging synchronization signal; and
a converting circuit configured to convert the image signal into a differential signal, and
the image processing processor comprises:
a display clock generating-circuit configured to generate a display clock;
a display synchronization signal generating circuit configured to generate a display synchronization signal based on the display clock;
a synchronization signal restoring circuit configured to restore the imaging synchronization signal from the synchronization superimposition signal,
a demodulating circuit configured to demodulate the differential signal into the image signal; and
a controller configured to compare a phase of the imaging synchronization signal with a phase of the display clock and control oscillation of the display clock generating circuit based on a result of the comparison.

2. The electronic endoscopic apparatus according to claim 1, wherein the imaging clock has a cycle that is M/N of a cycle of the display synchronization signal (where M and N are natural numbers).

3. The electronic endoscopic apparatus according to claim 1, wherein the image processing processor includes a synchronization memory configured to temporarily record the image signal, writing of the image signal into the synchronization memory is controlled based on the imaging synchronization signal, and read out of the image signal from the synchronization memory is controlled based on the display synchronization signal.

4. The electronic endoscopic apparatus according to claim 1, wherein the endoscopic scope comprises an electro-optic converting circuit configured to convert the image signal into an optical signal, and the image processing processor comprises a photoelectric converting circuit configured to convert the optical signal into the image signal.

5. The electronic endoscopic apparatus according to claim 1, wherein the endoscopic scope comprises a wireless transmitting circuit configured to wirelessly transmit the image signal, and the image processing processor comprises a wireless receiving circuit configured to receive the image signal that is wirelessly transmitted by the wireless transmitting circuit.

6. The electronic endoscopic apparatus according to claim 1, wherein the endoscopic scope comprises a compressing circuit configured to compress the image signal, and the image processing processor comprises a decompressing circuit configured to expand the image signal compressed by the compressing circuit.

7. The electronic endoscopic apparatus according to claim 1, wherein the endoscopic scope outputs scope type information indicating a type thereof; and the image processing processor comprises:
an identifying circuit configured to identify the type of the endoscopic scope with reference to the scope type information;
a second imaging clock generating circuit configured to generate a second imaging clock acting as a source of a second drive signal that drives the solid-state imaging device;
a second drive signal generating circuit configured to generate a second imaging synchronization signal and the second drive signal based on the imaging clock; and
an output controller configured to control whether or not to output the second imaging clock, the second imaging synchronization signal, and
the second drive signal to the endoscopic scope based on the type of the endoscopic scope which is identified by the identifying circuit.

8. The electronic endoscopic apparatus according to claim 1, wherein the endoscopic scope comprises a clock superimposing circuit configured to output a superimposition signal by superimposing the imaging clock on the image signal, and the image processing processor comprises a clock data restoring circuit configured to restore the imaging clock from the superimposition signal.

* * * * *